(12) United States Patent
Donovan et al.

(10) Patent No.: US 9,316,653 B2
(45) Date of Patent: Apr. 19, 2016

(54) USE OF SOLUBLE FORMS OF THE DESMOGLEIN I PROTEIN FOR THE PURPOSES OF SCREENING FOR ANTI-AGEING ACTIVE AGENTS

(75) Inventors: Mark Donovan, Berville (FR); Lucie Simonetti, Vincennes (FR); Dominique Bernard, Vanves (FR)

(73) Assignee: L'OREAL, Paris (FR)

( * ) Notice: Subject to any disclaimer, the term of this patent is extended or adjusted under 35 U.S.C. 154(b) by 761 days.

(21) Appl. No.: 12/687,601

(22) Filed: Jan. 14, 2010

(65) Prior Publication Data
US 2010/0216165 A1    Aug. 26, 2010

Related U.S. Application Data

(60) Provisional application No. 61/202,078, filed on Jan. 27, 2009.

(30) Foreign Application Priority Data

Jan. 13, 2009 (FR) ...................................... 09 50159

(51) Int. Cl.
G01N 31/00 (2006.01)
G01N 33/53 (2006.01)
G01N 33/68 (2006.01)
A61K 8/64 (2006.01)
A61Q 19/08 (2006.01)

(52) U.S. Cl.
CPC .............. *G01N 33/6881* (2013.01); *A61K 8/64* (2013.01); *A61Q 19/08* (2013.01); *G01N 2333/705* (2013.01); *G01N 2333/795* (2013.01)

(58) Field of Classification Search
CPC . A61K 38/00; G01N 33/566; G01N 33/6893; C07K 1/6886; C07K 14/705
See application file for complete search history.

(56) References Cited

U.S. PATENT DOCUMENTS

| 2003/0152599 A1 | 8/2003 | Maeda et al. |
| 2004/0142335 A1 | 7/2004 | Petersohn et al. |

FOREIGN PATENT DOCUMENTS

| EP | 1075835 | 2/2001 |
| FR | 2 925 312 | 6/2009 |
| JP | 2002/012512 | 1/2002 |
| JP | 2006 006143 | 1/2006 |
| WO | WO 02/053773 | 7/2002 |

OTHER PUBLICATIONS

Office Action as received in the corresponding Japanese Patent Application No. 2010-004447 dated Oct. 7, 2013 w/English translation.
U.S. Appl. No. 14/327,799, filed Jul. 10, 2014, Donovan, et al.
Office Action issued Aug. 20, 2014, in Chinese Patent Application No. 2014081500944930 (with English Translation).
A. Haratake et al., "Acceleration of de novo Cholesterol Synthesis in the Epidermis Influences Desquamation of the Stratum Corneum in Aged Mice" Skin Pharmacol Physiol, (2006), 19: 275-282.
A. Rawlings et al., The effect of glycerol and humidity on desmosome degradation in stratum corneum. Arch Dermatol Res (1995) 287: 457-464.

*Primary Examiner* — Lisa Cook
(74) *Attorney, Agent, or Firm* — Oblon, McClelland, Maier & Neustadt, L.L.P.

(57) ABSTRACT

The invention relates to the use of one or more complexed or noncomplexed, soluble peptide form(s) of Desmoglein I, as a marker for evaluating the effectiveness of active agents and/or of treatments, in particular anti-ageing active agents and/or treatments, with regard to an epidermis.

1 Claim, 1 Drawing Sheet

Figure 1:
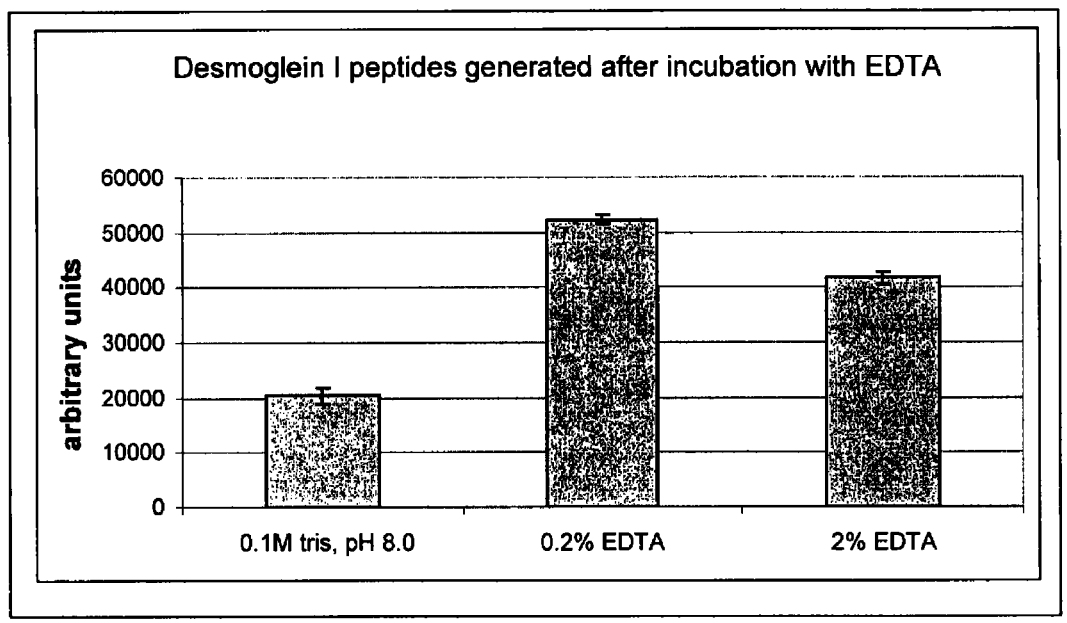

USE OF SOLUBLE FORMS OF THE DESMOGLEIN I PROTEIN FOR THE PURPOSES OF SCREENING FOR ANTI-AGEING ACTIVE AGENTS

This application claims the benefit of U.S. Ser. No. 61/202,078 filed Jan. 27, 2009 and FR 0950159 filed Jan. 13, 2009.

The present invention relates to the use of complexed or noncomplexed, soluble peptide forms which derive at least in part from Desmoglein I, for characterizing the effectiveness of potential active agents with regard to an epidermis showing one or more signs of skin ageing.

Epithelia are tissues of which the cells are joined to and interlinked with one another and lie on a basal membrane. They form either an external covering, for example at the surface of the skin, or the epidermis, or an internal covering, at the surface of a mucosa. They can also form glands.

More specifically, these epithelia are structures of which the homeostasis results from the implementation of a finely regulated set of intracellular and extracellular signals acting at all the stages of cell proliferation, migration and differentiation, and also of the synthesis of the various extracellular matrix components. These signals can in particular result from the action of factors produced by keratinocytes.

The maintaining of the correct physiological functions of an epithelium involves, in particular, epithelial terminal differentiation and/or proteoglycan synthesis.

As regards more particularly the epidermis, it is an epithelium, conventionally divided up into a basal layer of keratinocytes containing, in particular, skin stem cells and constituting the germinative layer of the epidermis, a "spiny" layer constituted of several layers of polyhedral cells placed on the basal layer, a "granular" layer comprising one to three layers said to be of flattened cells containing distinct cytoplasmic inclusions, keratohyalin granules, and finally, a set of upper cells, called horny layer (or stratum corneum) constituted of keratinocytes at the terminal stage of their differentiation, called corneocytes.

The stratum corneum, the outermost part of the skin which performs the function of a barrier between the organism and the environment, and the hair shaft, the emerging part of the hair follicle which constitutes the head of hair, both represent the result of the keratinocyte differentiation process. Epidermal differentiation follows a process of maturation in which keratinocytes from the basal layer differentiate and migrate so as to result in the formation of corneocytes, which are completely keratinised dead cells. This differentiation is the result of perfectly coordinated phenomena which will result in the thickness of the epidermis being kept constant and thus ensure the homeostasis of the epidermis.

Many skin disorders or pathological conditions can result from a dysfunction of epidermal homeostasis.

In the case of aged skin, this dysfunction is generally manifested through the appearance of wrinkles (microrelief and deep wrinkles), a loss of elasticity, a rough feel and dryness. From the histological point of view, a flattening of the dermo-epidermal junction and a decrease in thickness of the dermis and of the epidermis are observed. The collagen and glycosaminoglycan content decreases. The barrier function of the skin is impaired. All these phenomena are increased by chronic exposure to the sun.

Similarly, this dysfunction may be worsened in women during the menopause.

It is today known that these dysfunctions may in particular be associated with a different modulation of the expression and/or of the biological activity of certain proteins expressed in the stratum corneum. This is in particular the case of Desmoglein I.

Desmoglein I (also known as DGI) is a transmembrane glycoprotein comprising, in its preproprotein form, 1049 amino acids and having a molecular weight of approximately 114 kDa to 150 kDa, depending on whether or not it is glycosylated. In addition to the glycosylation sites on the asparagine residues at positions 36, 110 and 180, the sequence of this protein also comprises calcium-binding sites.

This protein is related to the cadherins and belongs to a family of proteins which also comprises Desmogleins II and III. DGI is present only in desmosomes, of which it is one of the major structural elements.

Document US 2004/0142335 reports, by means of a transcriptome analysis, an increase in the expression of the mRNA encoding the Desmoglein I protein in the skin of an elderly individual compared with that of a young individual. This document is silent to any soluble peptide form of Desmoglein I.

More recently, the inventors have, for their part, noted a significant increase in the expression of Desmoglein I, and therefore an accumulation of the latter, in the stratum corneum, during chronological ageing of the epidermis. The level of expression of Desmoglein I in the stratum corneum therefore constitutes a useful indication for characterizing the physiological condition of the skin, in particular in terms of ageing.

The present invention results, for its part, from the characterization by the inventors, in a human stratum corneum having undergone a desquamation-type treatment, of soluble peptide forms which are distinct from Desmoglein I but which clearly derive therefrom. It may be considered that the peptide forms characterized by the inventors are derived at least in part from the proteolysis of Desmoglein I.

In particular, a soluble peptide form of the invention is distinct from the whole sequence of Desmoglein I, namely SEQ ID NO 2.

As emerges from what follows, these complexed or noncomplexed, soluble peptide forms of this protein have been characterized by the inventors by virtue of the development of a specific ELISA assay technique, in particular described in Example 1, hereinafter.

Consequently, these soluble forms are found to be a particularly advantageous tool for screening for anti-ageing active agents, or even characterizing the effectiveness of a treatment for preventing and/or treating skin ageing in particular via an action, probably of degradation type, with regard to the accumulation of Desmoglein I in the stratum corneum, observed during skin ageing.

In the two cases, the effectiveness of the active agent or of the treatment under consideration is verified via an increase in the release of at least one, or even of several, of the soluble forms under consideration according to the invention.

Thus, according to one of its aspects, the present invention relates to the use of at least one complexed or noncomplexed, soluble peptide form which derives at least in part from a polypeptide having an amino acid sequence encoded by a nucleic acid sequence represented by all or part of SEQ ID No. 1, or an analogue thereof, as a tool for screening for active agents that are of use in preventing and/or treating skin ageing.

Accordingly, the present invention relates to a method for screening an active agent useful to prevent and/or treat skin ageing comprising a step of contacting at least one complexed or noncomplexed soluble peptide form which derives at least in part from a polypeptide having an amino acid sequence encoded by a nucleic acid sequence represented by all or part of SEQ ID No. 1, or an analogue thereof, with at least one active agent to be screened.

According to a preferred embodiment, a soluble peptide form suitable for the invention is not represented by sequence SEQ ID NO 2.

An increase in the amount of these soluble peptide forms is an indication of the effectiveness of an anti-ageing treatment.

In particular, detection of a presence or of an increase in a content of said peptide form(s) is indicative of an active agent with properties that are of use in preventing and/or treating skin ageing.

The present invention also relates to a method of screening for active agents, in particular anti-ageing active agents, comprising at least the steps consisting in:

a) bringing at least one cell type capable of releasing at least one soluble form in accordance with the invention into contact with at least one test anti-ageing active agent, under conditions suitable for release of said soluble peptide form, b) determining a content of said soluble peptide form, and c) comparing said content determined in step b) with a content of said soluble form determined in the absence of test chemical or biological compound.

Advantageously, a step of selecting the active agent(s) for which an increase in the content of soluble form(s) is observed may also be carried out, at the end of step c).

According to another of its aspects, the present invention is also directed towards a noninvasive, in particular cosmetic, method for characterizing the effectiveness of a cosmetic or therapeutic treatment intented, in an individual, to prevent and/or treat the signs of skin ageing linked to chronological ageing, such as wrinkles and fine lines, comprising at least the qualitative or quantitative characterization of at least one soluble peptide form of Desmoglein I according to the invention.

In particular, according to a method of the invention, detection or characterization of the presence or of an increase in a content of said peptide form reflects an effectiveness of said active agent or of said treatment.

According to one embodiment, one of the methods defined above may also comprise, at the end of the step of characterizing of at least one soluble peptide form of Desmoglein I, at least one additional step consisting in administering, to the individual thus evaluated, a care, in particular cosmetic, composition established or selected with regard to the information obtained on said soluble form. In particular, said additional step may be consecutive to the characterization step.

According to one embodiment, such a composition may be selected from a range of compositions, each being suitable for a type of information that can be obtained at the end of the characterization step.

Thus, the advantage of the present invention is to propose a simple and rapid method, firstly, for characterizing a physiological state of an epithelium, and in particular of the epidermis of the skin, and secondly, for adjusting accordingly a treatment suitable for said epithelium or epidermis.

The expression "signs of skin ageing" is intended to mean all the modifications of the external appearance of the skin due to chronological ageing, for instance wrinkles and fine lines, wizened skin, lack of elasticity and/or of tonicity of the skin, thinning of the dermis and/or degradation of the collagen fibres, thereby leading to the appearance of slack and wrinkled skin.

More specifically, the nontherapeutic method as defined above aims to characterize the effectiveness of a treatment capable of preventing and/or treating the signs of skin ageing in an individual, comprising at least the steps consisting in:

i. providing at least a first skin surface sample representative of said individual, ii. quantifying, in said sample, especially via an ELISA assay technique, in particular as described in Example 1 hereinafter, at least one soluble peptide form according to the invention, iii. repeating steps i. and ii. on a second skin surface sample representative of said individual, and iv. comparing the results obtained at the end of steps ii. and iii., in particular in order to deduce therefrom information relating to at least one effect of the treatment, said first and second skin surface samples corresponding to different treatment stages.

The reference value or piece of data in step ii. may be a piece of data obtained from the epithelium, in particular from the epidermis, representative of the individual who is the subject of the treatment, prior to the administration of said treatment.

According to one preferred embodiment, the first sample is representative of a pretreatment state and the second is representative of a state during the course of treatment or a post-treatment state.

Detection, in step iv., of the presence or of an increase in a content of said soluble peptide form reflects an effectiveness of said treatment.

According to yet another embodiment, a method of the invention may further comprise a step consisting in adjusting said treatment, in said individual, by administration of a cosmetic care composition established or selected with regard to the information obtained at the end of step iv.

According to yet another aspect, the present invention also relates to the use of at least one soluble peptide form in accordance with the invention, as a tool for screening for biological or chemical compounds capable of acting with respect to Desmoglein I, and in particular of degrading it, and consequently capable of inducing and promoting the release of the soluble forms of Desmoglein I.

Accordingly, the present invention relates to a method for screening for an active biological or chemical compound capable of promoting the release of the soluble forms of Desmoglein I, comprising a step of contacting at least one complexed or noncomplexed soluble peptide form which derives at least in part from a polypeptide having an amino acid sequence encoded by a nucleic acid sequence represented by all or part of SEQ ID No. 1, or an analogue thereof, with at least one active biological or chemical compound to be screened The characterization of the soluble forms may also prove to be useful for establishing a diagnosis of the state of an epidermis.

Thus, the present invention relates to the use of a soluble peptide form according to the invention, as a tool for the in vitro or ex vivo characterization of a state of an epithelium, in particular of a state of chronological ageing of an epithelium, the detection of the presence or of a decrease in a content of said peptide form(s) being indicative of a state of chronological ageing of an epithelium.

Accordingly, the present invention relates to a method for the in vitro or ex vivo characterization of a state of chronological ageing of an epithelium, comprising a step of contacting at least one complexed or noncomplexed soluble peptide form which derives at least in part from a polypeptide having an amino acid sequence encoded by a nucleic acid sequence represented by all or part of SEQ ID No. 1, or an analogue thereof, with at least one epithelium to be characterized.

According to another of its aspects, the present invention relates to a noninvasive, in particular cosmetic, method for characterizing, in particular in vitro or ex vivo, the chronological state of an epidermis, comprising at least the qualitative or quantitative characterization of soluble peptide forms of Desmoglein 1 according to the invention.

This method of characterization of a state of an epithelium comprises at least the steps consisting in:

a) determining, in a surface sample of said epithelium, especially via an ELISA assay technique, a content of at least one soluble peptide form in accordance with the invention, and b) comparing said content determined in step a) with a reference value.

According to one variant of implementation, the piece of data or value obtained can be assessed in comparison with a reference piece of data or value, obtained, for example, from at least one epithelium, in particular an epidermis, distinct from that which is the subject of the characterization, and the state of which is known.

The methods of the invention may be carried out in vitro, ex vivo or in vivo.

As emerges from the description that follows, the methods according to the invention are particularly advantageous insofar as the implementation thereof does not require an invasive procedure.

This is because the localisation, by the inventors, of these new biomarkers in the stratum corneum makes it possible to carry out a quantitative or qualitative characterization of the expression of said markers by simply taking a sample topically.

Advantageously, it may be carried out on a sample of stratum corneum of the individual under consideration, simply taken by stripping. The sampling method may, for example, be a stripping technique consisting in applying a portion of adhesive tape to the epithelium under consideration, such as an epidermis. When detaching this adhesive tape, a fraction of the epithelium, for example an epidermal fraction, is removed. After protein extraction, said fraction is subsequently analysed by means of an ELISA assay as considered in the present invention.

According to yet another aspect, the present invention relates to the use of an effective amount of soluble peptide form(s) in accordance with the invention, for preparing and/or improving a pluristratified cell model, in particular a model of reconstructed skin.

For the purpose of the present invention, the expression "effective amount" is intended to denote the minimum amount necessary for obtaining the expected effect.

According to yet another aspect, the present invention relates to a method of preparing an isolated reconstructed skin, comprising at least the step consisting in bringing at least one soluble peptide form according to the invention into contact with cells capable of generating an isolated reconstructed skin, and in particular keratinocytes.

Definition of "Soluble Forms" of Desmoglein I

For the purpose of the present invention, the term "soluble" is intended to describe the ability of the complexed or non-complexed peptide form, under consideration according to the invention, to solubilise in water or in an aqueous medium without protein-denaturing substances, such as chaotropic agents or ionic detergents for example, as opposed to native Desmoglein I, which can be extracted only in the presence of such agents.

For the purpose of the present invention, the term "complexed" refers to a soluble conjugate of one of the peptide forms under consideration according to the invention, with either a protein distinct from Desmoglein I or a fragment of this protein, or another soluble form of the Desmoglein I protein or a derivative thereof.

For the purpose of the present invention, the term "derivative of the Desmoglein I protein" denotes a fragment thereof or an analogue, as defined hereinafter.

These soluble complexed forms may be the product resulting from the association of the Desmoglein I protein or a fragment thereof, with a secondary protein, also called target protein.

By way of illustration of these proteins capable of interacting with Desmoglein I and/or a fragment thereof, mention may in particular be made of desmocollin 2a (Dsc2), Plakophilins 1, 2 and 3, Plakoglobin, Kallikrein 5, growth hormone 1 (GH1), SSSCA1 (27 kD centromeric autoantigen), RuvB-like 1, C3orf10 protein and VRK3 (vaccinia related kinase 3).

As previously specified, the soluble forms in accordance with the invention derive, at least in part, from the proteolysis of a polypeptide having an amino acid sequence encoded by a nucleic acid sequence represented by all or part of SEQ ID No. 1, or an analogue thereof.

For the purpose of the present invention, the expression "fragment of a nucleic acid sequence" is intended to denote a nucleic acid sequence partly encoding the polypeptide from which the soluble forms in accordance with the invention, or analogues thereof, derive, and in particular a nucleic acid sequence represented by SEQ ID No. 1 or an analogue thereof.

The expression "analogue of a nucleic acid sequence" is intended to denote any nucleic acid sequence optionally resulting from the degeneracy of the nucleic acid code, and in part encoding soluble forms having a sequence identical or analogous to those in part encoded by said nucleic acid sequence.

The nucleic acid sequences may be derived from all possible origins, i.e. either animal, in particular mammalian, or even more particularly human, or plant, or from microorganisms (viruses, phages, bacteria, inter alia) or alternatively from fungi, without prejudging the fact that they may or may not be present naturally in said organism of origin.

According to another embodiment, the soluble forms in accordance with the invention derive at least in part from the proteolysis of the polypeptide having the amino acid sequence represented in SEQ ID No. 2, or an analogue thereof.

For the purpose of the present invention, the term "Desmoglein I" is intended to denote, in general, unless otherwise indicated, the sequence (SEQ ID No. 2) of the protein which may or may not have undergone post-translational modifications, of N-acetylglycosylation type on the asparagine residues in position 36, 110 or 180, capable of modifying its apparent molecular weight or its isoelectric point.

It is, moreover, known that the primary sequence of a polypeptide, i.e. the series of amino acids, determines sites specifically recognised by protease enzymes, such as trypsin, which, once the recognition of these sites has become effective, will induce cleavage of the polypeptide by proteolysis. This proteolysis results in the generation of various peptides, or proteolytic fragments, which, when they are in a soluble form, prove to be representative of the soluble peptide forms of Desmoglein I under consideration according to the invention.

Thus, according to one particular embodiment, the polypeptide from which the soluble forms in accordance with the invention are derived has an amino acid sequence chosen from SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32, SEQ ID No. 33, SEQ ID No. 34, SEQ ID No. 35, SEQ ID No. 36, SEQ ID No. 37, SEQ ID No. 38, SEQ ID No. 39, SEQ ID No. 40, SEQ ID No. 41, SEQ ID No. 42, SEQ ID No. 43, SEQ ID No. 44, SEQ ID No. 45, SEQ ID No. 46, SEQ ID No. 47, SEQ ID No. 48, SEQ ID No. 49, SEQ ID No. 50, SEQ ID No. 51, SEQ ID No. 52, SEQ ID No. 53, SEQ ID No. 54, SEQ ID No. 55, SEQ ID No. 56, SEQ ID No. 57, SEQ ID No. 58, SEQ ID No. 59, SEQ ID No. 60, SEQ ID No. 61, SEQ ID No. 62, SEQ ID No. 63, SEQ ID No. 64, SEQ ID No. 65, SEQ ID No. 66, SEQ ID No. 67, SEQ ID No. 68, SEQ ID No. 69, SEQ ID No. 70, SEQ ID No. 71, SEQ ID No. 72, SEQ ID No. 73, SEQ ID No. 74, SEQ ID No. 75, SEQ ID No. 76, SEQ ID No. 77, SEQ ID No. 78, SEQ ID No. 79, SEQ ID No. 80, SEQ ID No. 81, SEQ ID No. 82, SEQ ID No. 83, SEQ ID No. 84 and SEQ ID No. 85, and mixtures thereof.

The term "analogue of a polypeptide" is intended to denote any polypeptide exhibiting a sequence homology, in particular with respect to one of the characteristic sequences of said polypeptide, and also a biological activity of the same nature. This analogue may be a peptidomimetic agent.

The homology may be at least 85%, for example at least 90%, and for example at least 95%. The homology may be determined by visual comparison or by means of any computer tool generally used in the field, such as the BLAST programs available at www.ncbi.nlm.nih.gov, and used with the default parameters.

The sequence homology may result from modifications derived from mutation or variation in the sequences of the peptides according to the invention, originating either from the deletion or from the insertion of one or more amino acids, or from the substitution of one or more amino acids in the characteristic sequences of a polypeptide according to the invention.

For the purpose of the invention, the term "fragment" is intended to denote any peptide portion comprising at least 4, at least 6, in particular at least 8, and more particularly at least 12 consecutive amino acids of Desmoglein I, and a substantially similar biological activity. In general, the polypeptide analogues may comprise conservative substitutions with respect to the natural amino acid sequence.

Several of these modifications may be combined.

By way of example of mutations that may be considered in the present invention, mention may be made, nonexhaustively, of the replacement of one or more amino acid residues with amino acid residues having a similar hydropathic index, without, however, substantially affecting the native biological properties of Desmoglein I.

The hydropathic index is an index assigned to amino acids according to their hydrophobicity and their charge (Kyte et al. (1982), J. Mol. Biol., 157: 105).

The soluble forms that are also covered by the present invention may derive from polypeptides having undergone one or more post-translational modification(s).

The term "post-translational modification(s)" is intended to encompass all the modifications that a peptide or a protein is capable of undergoing at the end of the synthesis thereof in a cell, such as, for example, one or more phosphorylation(s), one or more thiolation(s), one or more acetylation(s), one or more glycosylation(s), one or more lipidation(s), such as a farnesylation or a palmitoylation, a structural rearrangement such as the formation of disulphide bridges and/or cleavage within the peptide sequence.

The analogue has, moreover, substantially the same biological activity as the natural polypeptide.

According to one embodiment, the soluble forms suitable for the implementation of the invention may also be natural or synthetic polypeptides, obtained after enzymatic or chemical lysis of the native form of Desmoglein I or by chemical or biological synthesis or by extraction from a biological tissue, for instance the skin, naturally expressing these soluble forms, and also the various post-translational forms thereof.

According to one embodiment, a complexed soluble form in accordance with the invention may derive from the association of Desmoglein I, or of a fragment thereof, with either another Desmoglein I protein or a fragment thereof, or a target protein.

A target protein may in particular be chosen from desmocollin 2a (Dsc2), Plakophilins 1, 2 and 3, Plakoglobin, Kallikrein 5, growth hormone 1 (GH1), SSSCA1 (27 kD centromeric autoantigen), RuvB-like 1, the C3orf10 protein and VRK3 (vaccinia related kinase 3).

Those skilled in the art may obtain the soluble forms in accordance with the invention by means of recombinant DNA-based methods, for instance those described in the manual "Molecular Cloning—A Laboratory Manual" (2$^{nd}$ edition), Sambrook et al., 1989, Vol. I-III, Coldspring Harbor Laboratory, Coldspring Harbor Press, NY, (Sambrook).

According to another embodiment, the soluble forms suitable for the implementation of the invention may also be in a form fused with another polypeptide distinct from those identified above, a hydrophilic or hydrophobic targeting agent, a bioconversion precursor, or a luminescent, radioactive or colorimetric labelling agent.

In a nonlimiting manner, mention may be made, as an example of compounds that can be coupled with the soluble forms in accordance with the invention, of fluorescent proteins such as the "Green Fluorescent Protein", fluorescent chemical compounds such as rhodamine, fluorescein or Texas Red®, phosphorescent compounds, radioactive elements such as $^{3}H$, $^{14}C$, $^{35}S$, $^{121}I$ or $^{125}I$, or colorimetric labelling agents such as chromogenic substrates sensitive to the action of galactosidase, of peroxidase, of chloramphenicol acetyl transferase, of luciferase or of alkaline phosphatase.

Depending on the nature of the compounds that can be coupled with the soluble forms in accordance with the invention, the coupling may be performed by chemical methods, in particular by means of reactive chemical functions, or by molecular biology methods known to those skilled in the art.

By way of methods for detecting a polypeptide, mention may be made of Western blotting, Slot blotting, Dot blotting, ELISA (Enzyme Linked Immuno-Sorbent Assay) methods of singleplex or multiplex type, proteomics or glycomics methods, staining of polypeptides in a polyacrylamide gel with a silver-based stain, with Coomassie blue or with SYPRO, immunofluorescence, UV absorption, immunohistochemical methods in conventional, electron or confocal microscopy, FRET (fluorescence resonance energy transfer), TR-FRET (time-resolved FRET) methods, FLIM (fluorescence lifetime imaging microscopy) methods, FSPIM (fluorescence spectral imaging microscopy) methods, FRAP (fluorescence recovery after photobleaching) methods, reporter-gene methods, AFM (atomic force microscopy) methods, surface plasmon resonance methods, microcalorimetry methods, flow cytometry methods, biosensor methods, radioimmunoassay (RIA) methods, isoelectric focusing methods, and enzymatic assays, methods using peptide chips, sugar chips, antibody chips, mass spectrometry methods, and SELDI-TOF spectrometry methods (Ciphergen).

As emerges from the above, the soluble forms under consideration according to the invention are advantageously characterized by means of an ELISA method, and more particularly by means of that described in Example 1 hereinafter.

Use of the Soluble Forms According to the Invention for the Purposes of Screening for Anti-Ageing Active Agents and/or of Characterizing the Effectiveness of a Treatment Against the Signs of Skin Ageing As specified above, according to one of its aspects, the present invention relates to noninvasive methods for characterizing, in particular in an in vitro or ex vivo manner, the effectiveness of an anti-ageing active agent or of a cosmetic or therapeutic treatment, via the analysis, qualitatively or quantitatively, of the soluble forms in accordance with the invention.

These methods are particularly advantageous insofar as the implementation thereof does not require obligatory recourse to a surgical technique in order to carry out such a characterization.

The methods according to the invention, described hereinafter, can be carried out on a sample, for example an isolated sample, of epithelium, and in particular of epidermis, taken from an individual.

The methods according to the invention may also be carried out on a sample of epithelium, and in particular of epidermis, taken from an epithelial cell, and in particular epidermal, model or from a reconstructed isolated skin in order to define the state thereof.

An extract of the epidermis may thus be obtained by simple stripping, and directly analysed by the ELISA method as described in Example 1 hereinafter.

The stripping technique consists in applying a sticky surface to the surface of the epidermis, such as Blenderm® from 3M, D'squam (commercial adhesive from CuDERM), or cyanoacrylate glue. By virtue of these strippings, the adherent corneocytes and the content of their intercellular spaces can be sampled and subsequently subjected to an extraction which makes it possible to access the protein content.

The taking of a sample suitable for the method may also be carried out more directly by "washing" the skin surface by means, for example, of accessories of the vane turbine type or of the spiral cell type (as described in patent FR 2 667 778) combined with a fluid circuit, or simply by addition/removal of a drop of buffer at the surface of the skin.

By way of indication of other sampling methods suitable for implementing the invention, mention may be made of methods based on scraping the upper part of the stratum corneum by means of a twin blade system or by shave biopsy. This technique makes it possible to collect squamae which can then be directly analysed by various techniques in order to determine the mineral, amino acid or lipid contents.

At the end of the sampling, the sample is characterized by the ELISA method considered in Example 1, hereinafter.

This method is based in particular on the use of antibodies that are suitable for the detection of soluble forms under consideration according to the invention.

An antibody that can be used as a tool for evaluating a state of an epidermis may be obtained by any method known to those skilled in the art, as described in "Antibodies: A Laboratory Manual", Cold Spring Harbor Laboratory Press, Cold Spring Harbor, N.Y. (1990). Advantageously, the antibodies used may be recombinant antibodies such as those developed by the company Antibodies-by-design (AbD).

As described in Example 1 hereinafter, the method of detecting the soluble forms of Desmoglein I requires in particular the use of two antibodies, i.e. a capture antibody developed with the HuCAL technology (AbD clone AbyD03984) and a detection antibody labelled with "sulpho-tag" according to the MSD indications (monoclonal antibody, clone 129204, R&D systems).

Screening for Biological or Chemical Compounds

The present invention relates to a method of screening for biological or chemical compounds, or even anti-ageing active agents, or physicochemical factors, capable of acting on Desmoglein I and, consequently, of influencing the release of the soluble forms in accordance with the invention, comprising at least the steps consisting in:

a) bringing at least one cell type capable of releasing at least one soluble peptide form in accordance with the invention into contact with at least one test chemical or biological compound, under conditions suitable for the release of said soluble peptide form, b) determining a content of said soluble peptide form, and c) comparing said content determined in step b) with a content of said soluble form determined in the absence of test chemical or biological compound.

Advantageously, a step of selecting the active agent(s) for which an increase in the content of soluble form(s) is observed may also be carried out, at the end of step c).

The comparison carried out in step c) may make it possible to deduce information as to the property of said tested compound of modifying Desmoglein I, and therefore of influencing the release of the soluble forms in accordance with the invention.

In this respect, a compound exhibiting an effectiveness with regard to Desmoglein I, which accumulates with age in the stratum corneum, induces the release of soluble forms of Desmoglein I in accordance with the invention.

Detection of the presence or an increase in the content of said soluble peptide form is indicative of a chemical or biological compound capable of acting on Desmoglein I.

More particularly, the method that is of use for characterizing the effectiveness of a treatment capable of preventing and/or treating the signs of skin ageing in an individual, may comprise at least the steps consisting in:

i. providing at least a first skin surface sample representative of said individual, ii. quantifying, in said sample, in particular via an ELISA assay technique, at least one soluble form under consideration in the present invention, iii. repeating steps i. and ii. on a second skin surface sample representative of said individual, and iv. comparing the results obtained at the end of steps ii. and iii., in particular in order to deduce therefrom information relating to at least one effect of the treatment, said first and second skin surface samples corresponding to different treatment stages.

In the event that a reference value measurement is carried out prior to the use of the biological or chemical compound, or even of an anti-ageing active agent, or of the physicochemical factor to be tested, the method according to the invention may also make it possible, where appropriate, to assess the potential effectiveness of said compound.

The release of soluble form(s) in accordance with the invention may not be affected by the presence of said compound or, on the other hand, be stimulated.

In the event that a stimulatory effect is observed, the compound tested is capable of being used, for example as an anti-ageing active agent.

A method in accordance with the invention may be carried out on an isolated cell sample.

The determination of a content of the soluble forms in accordance with the invention is carried out by means of the specific ELISA method as described in Example 1 hereinafter.

The present invention also relates to the use of an effective amount of soluble forms in accordance with the invention, for preparing and/or improving a pluristratified cell model, especially of epidermal or mucosal type, and in particular a reconstructed skin model.

For the purpose of the invention, the term "reconstructed skin model" is intended to denote a model in which various cell types, such as, in particular, the natural constituents of the skin, for example keratinocytes, fibroblasts, Langerhans cells and melanocytes, are combined.

Fibroblast-type cells may or may not be irradiated.

Such models and the preparation thereof are known to those skilled in the art.

Thus, the present invention is also directed towards a method of preparing an isolated reconstructed skin, comprising at least the step consisting in bringing at least one soluble form in accordance with the invention into contact with cells capable of generating an isolated reconstructed skin, and in particular keratinocytes.

For the purpose of the present invention, according to another of its aspects, the soluble forms of Desmoglein I as described above may be used in a cosmetic or therapeutic composition.

It is understood that all the cosmetic or therapeutic compositions under consideration according to the invention use a physiologically acceptable medium.

For the purpose of the present invention, the term "physiologically acceptable medium" is intended to denote a medium suitable for the application of a composition to an epithelium or a keratin material, such as the skin, the scalp, the lips, the mucous membranes and keratin fibres such as the hair, the nails and body hair, or, where appropriate, orally or parenterally.

According to one particular embodiment, the invention may be in the form of a cosmetic or therapeutic composition.

A composition in accordance with the invention may comprise, in addition to the soluble form(s), at least one cosmetic and/or therapeutic active agent.

As examples of active agents that can be used in the context of the present invention, mention may be made of cosmetic oils, such as silicone oils, plant oils of triglyceride type, hydrocarbon-based oils such as parleam oil and esters of fatty acids and of fatty alcohols.

Other active agents for improving the condition of the skin may also be used, such as moisturising active agents or active agents for improving the natural lipid barrier, such as ceramides, cholesterol sulphates and/or fatty acids, and mixtures thereof.

It may also be possible to use enzymes which have an activity on the skin, such as proteases, lipases, glucosidases, amidases, cerebrosidases and/or melanases, and mixtures thereof.

In general, any composition in accordance with the invention may be applied to the skin (on any cutaneous region of the body) or to the mucous membranes (buccal, jugal, gingival, genital, conjunctival, etc.).

In a known manner, a cosmetic composition may also contain adjuvants which are customary in the cosmetics field, such as hydrophilic or lipophilic gelling agents, hydrophilic or lipophilic additives, preservatives, antioxidants, solvents, fragrances, fillers, screening agents, odour absorbers and dyestuffs.

The amounts of the various constituents of the compositions according to the invention are those conventionally used in the fields under consideration.

According to another aspect, the present invention relates to a method for the cosmetic treatment of the signs of skin ageing, comprising at least one step consisting in applying at least one cosmetic composition in accordance with the invention to at least a part of the skin, the mucous membranes and/or the keratin fibres.

According to another aspect, the invention also relates to the use, in particular cosmetic and/or therapeutic use, of soluble peptide forms of Desmoglein I, or of analogues thereof, or of an agent which modulates the activity, the expression and/or the stability of such a polypeptide, in particular for preventing the signs of skin ageing, in particular for preventing and/or treating aged skin.

According to another embodiment, the invention relates to the use of an agent which modulates the soluble forms in accordance with the invention.

For the purpose of the invention, the term "modulate" is intended to mean, from the viewpoint of a given effect, the action of stimulating or inhibiting this effect.

For the purpose of the present invention, the expression "agent which modulates or chemical or biological compound capable of modulating the biological activity and/or the expression" is intended to mean any compound capable of acting, directly or indirectly, on the soluble forms in accordance with the invention, or a nucleic acid sequence partly encoding said soluble forms, or on an element of an intracellular or extracellular signalling pathway, or of a metabolic pathway, involving said soluble forms, or on an element involved in regulating the transcription and/or the translation of a nucleic acid sequence encoding said soluble forms, and also in regulating the stability of said soluble forms.

This modulating agent may be an agent which inhibits or activates the expression of the soluble forms of the invention, or else an agent which regulates the stability of said soluble forms.

More particularly, the modulating agent may be an activator of the expression of the soluble forms according to the invention.

According to one preferred embodiment, the modulating agent is an agent which promotes the stability of the soluble forms in accordance with the invention, by inhibiting the proteolytic degradation thereof.

The examples which appear hereinafter are presented by way of nonlimiting illustration of the invention.

FIG. 1: it illustrates the effectiveness of the high-sensitivity ELISA assay in accordance with the invention in the monitoring of active agents which act on the degradation of Desmoglein I.

Figure 2:
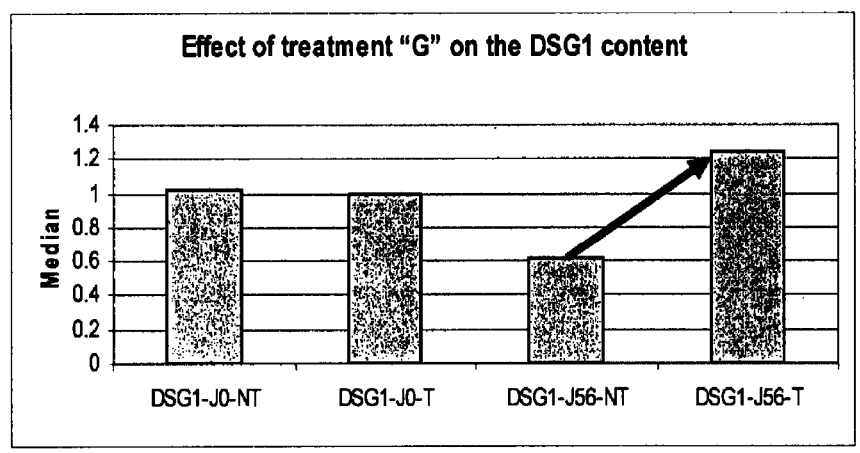

FIG. 2: it illustrates the effects of a serum composed of 10% of bifidiobiotic (CLR complex) and 0.002% of phytosphingosine-SLC (treatment "G") on the amount of soluble peptide forms in accordance with the invention.

EXAMPLE 1

Development of a High-sensitivity ELISA Assay for Assaying Soluble Forms of Desmoglein I in Accordance with the Invention:

"Desmoglein"-specific 96-well plates were developed custom-made with the technology of the company MesoScale Discovery (MSD).

The recombinant capture antibody (clone AbyD03984), directed against an extracellular domain of the Desmoglein was developed with the HuCAL technology (company: Antibodies by Design) by means of a screening carried out with a recombinant Desmoglein (R&D systems).

The capture antibody was deposited at a concentration of 200 µg/ml on a standard 96-well plate of small spot type (MesoScale).

A reference curve (400 to 6 ng/ml) was established using a recombinant Desmoglein protein. Each plate was blocked with a blocking buffer (MesoScale) for 1 hour at ambient temperature. 25 µl of each sample and of standards were deposited in triplicate and incubated with stirring for 1 hour at ambient temperature. The plate was then washed 4 times with Tris buffer (MesoScale). The plates were then incubated with stirring for 1 hour at ambient temperature with 25 µl of detection antibody (monoclonal antibody, clone 129204, R&D Systems) labelled with "sulpho-tag" according to the MSD indications at a concentration of 1 ug/ml. The plates were washed 4 times with a Tris buffer (MesoScale) before the addition of 150 µl of 1× read buffer T (MesoScale). The plates were read using the "Sector Imager 6000". The data were standardised in terms of ng of Desmoglein per µg of total protein, measured using a Bradford kit (Bio-Rad).

EXAMPLE 2

Use of the High-sensitivity ELISA Assay for Screening for Active Agents which Act on the Degradation of Desmoglein I.

Protocol:

6 mg of finely ground plantaire Stratum Corneum (PSC) are distributed into each well of a 96-well Multiscreen 0.22 μm filtration system plate (Millipore). Each assay is carried out in triplicate.

100 μl of EDTA at 0.2 and 2% in 0.1M Tris buffer, pH 8, are added to the PSC. The plate is incubated for 10 min at ambient temperature. The plate is then filtered, and the wells are rinsed 5 times with 200 μl of PBS buffer. 200 ml of 0.1M Tris buffer, pH 8, are added to each well. The plate is incubated for 2 h with stirring at 30° C. and then filtered into a reception plate. Each reaction medium is thus collected.

The Desmoglein I peptides are assayed on a Mesoscale MA6000 DB016 plate, the development of which has been previously described.

Each assay is carried out directly with 25 μl of reaction medium. A standard range is prepared under the same conditions with recombinant Desmoglein (R&D systems). The results can be expressed either in AU (arbitrary units=signal obtained on the "sector imager 6000") or in ng of Desmoglein I per μg of total proteins.

FIG. 1 makes it possible to actually monitor the release of soluble forms of Desmoglein I, induced by a treatment which promotes degradation of the corneodesmosome, such as a treatment with chelators of the EDTA family.

The assay is therefore suitable for evaluating a Desmoglein I degradation-stimulating effect by measuring the soluble forms released in vitro.

This assay is therefore indicated for monitoring the effect of molecules or of cosmetic formulations, in particular of anti-ageing active agents, which make it possible to compensate for the abnormal accumulation of Desmoglein I observed in the aged stratum corneum.

EXAMPLE 3

Characterization of the Content of Soluble Forms of Desmoglein I in Various Samples Taken by Stripping This characterization is carried out using the ELISA assay described in Example 1.

A product study was carried out over 56 days, i.e. 2 months (1 group of 24 female individuals, with Caucasian skin, aged 40-45), with samples taken on the forearm.

The product is a serum made up of 10% of Bifidiobiotic (CLR complex) and 0.002% of Phytosphingosine-SLC (treatment "G").

The CLR complex relates to a lysate registered under the INCI name: Bifidat ferment Lysate, under the EINECS name: Bifidobacterium longum, under EINECS No.: 306-168-4 and under CAS No.: 96507-89-0.

Such a lysate is in particular sold under the name Repair Complex CLR® by the company K. Richter GmbH. The phytosphingosine-salicylate derivative is that sold by the company Evonick Goldschmidt under the name Phytosphingosine SLC.

For this study, D-squame samples were taken from the forearm (posterior face).

a) Extraction of the Proteins from the D-Squame Corneodiscs:

The corneodisc is placed in a 2 ml Eppendorf tube, sticky surface facing inwards, to which 550 μl of "Native+" extraction buffer (TBS, 1% TRITON™ X-100, 1M NaCl) and one stainless steel bead per tube are added. The tube is then placed in the racks of a MM400 vibration mill (Retsch). The extraction is carried out by vibration milling for one cycle of 2 min at 30 Hz. The medium is then recovered and filtered through a 0.45 μm Millipore Ultrafree column, followed by centrifugation at 5000 g at 4° C. for 5 min. The supernatant is stored at −20° C. while awaiting to be analysed.

b) Statistical Analysis

The analysis, for the treatment effect, is carried out using a mixed model of analysis of variance on the paired active agent-placebo differences with the time factor as fixed effect, and the subject factor as random effect.

The treatment effect at D0 and D56 is tested by means of contrasts.

The variables are, when necessary, log-transformed beforehand so as to render their distribution more Gaussian.

The SPSS software, version 14, is used for the descriptive analyses (graphs of the means and box plots) and the SAS Enterprise Guide software, version 3 for the interference part.

The first-species alpha-risk is fixed at 5% in a two-sided approach.

The results of this study are illustrated in FIG. 2.

FIG. 2 reveals the effect of the tested product on the amount of soluble forms. A significant increase in the release of soluble forms of Desmoglein I is observed, thereby demonstrating the stimulatory effect of this product on the release of Desmoglein I.

The tested product therefore has a real anti-ageing effect since it makes it possible to counteract the accumulation of Desmoglein I with age.

The invention claimed is:

1. A method for characterizing the effectiveness of a cosmetic treatment intended, in an individual having an epidermis showing one or more signs of skin ageing, to compensate the accumulation of desmoglein I in the stratum corneum, the method comprising:

a) after administering the cosmetic treatment, obtaining a skin sample from the individual;
   b) quantifying at least one soluble peptide form with an anti-desmoglein I antibody, wherein the soluble peptide derives at least in part from the proteolysis of a polypeptide comprising an amino acid sequence represented by part of SEQ ID NO:2; and
   c) comparing the content obtained in step b) with a reference value obtained from a cosmetically untreated skin sample, and the presence or increase in the soluble peptide form content with respect to the reference value being indicative of a release of desmoglein I from the stratum corneum, and said release of desmoglein I being indicative of an effectiveness of the cosmetic treatment.

* * * * *

SEQUENCE LISTING

```
<160> NUMBER OF SEQ ID NOS: 85

<210> SEQ ID NO 1
<211> LENGTH: 4512
<212> TYPE: DNA
<213> ORGANISM: Homo Sapiens

<400> SEQUENCE: 1
cccagcccaa gtttttaggg tggggatcca gactggttat acgtaccttc agtccttctc      60
ccagaggaag gcagaaacac ctcaaagcct gcatgtaaga acatctactg agaaattatt     120
```

```
ttaatcagac accagctgag tgggagaaag gaaaagaaca gagaagaaca aacaaaactc      180
ccttggtctt ggatgtaaga gaatccagca gagatggact ggagtttctt cagagtagtt      240
gcagtgctgt tcattttct ggtggtggta gaagttaaca gtgaattccg aatccaggta       300
agagattata acactaaaaa tggcaccatc aaatggcatt caatccgaag gcagaaacgt      360
gaatggatca agttcgcagc agcctgtcgt gaaggtgaag acaactcaaa gaggaaccca      420
atcgccaaaa ttcactcaga ttgtgctgca aaccagcaag ttacataccg catctctgga     480
gtaggaattg atcagccacc atatgggatc tttgtcatta atcagaaaac tggtgaaatt     540
aatataacat ccatagttga tcgagaggtc actcctttct tcattatcta ctgccgagct    600
ctgaactcaa tgggccaaga tttagagagg cctctagagc tcagagtcag ggttttggat    660
ataaatgaca accctccagt gttttcaatg gctacatttg caggacaaat agaagaaaat    720
tctaatgcaa atacactggt gatgatactc aatgctactg acgcagatga accgaacaat   780
ttgaactcaa aaatagcctt caagattata agacaagaac cttcagattc accaatgttt   840
attatcaaca gaaatactgg agaaattcga acgatgaata attttctaga cagagagcaa   900
tacggccagt atgctcttgc tgtaagaggc tctgaccgag atggtggggc agatggcatg   960
tcagcggaat gtgagtgcaa cattaaaatc ctcgatgtca atgataatat cccttacatg  1020
gaacagtctt catataccat agaaattcaa gaaaatactc taaattcaaa tttgctcgag  1080
attagagtaa ttgatttgga tgaagagttc tcagctaact ggatggcagt aattttcttt   1140
atctctggaa atgaaggaaa ttggtttgag atagaaatga atgaaagaac aaatgtggga   1200
attttaaagg ttgttaagcc cttagattat gaagctatgc agagtctgca actcagtatt   1260
ggtgtcagaa ataaagctga atttcatcat tcaattatgt ctcaatataa actgaaagca   1320
tctgcaattt ctgtgactgt gttaaatgta attgaaggcc cagtgtttcg tccaggttca   1380
aagacatatg ttgtaactgg taatatggga tcaaatgata aagtgggaga ctttgtagct   1440
actgacctgg acacaggtag accttcaacg actgttaggt atgtaatggg aaataatcca   1500
gctgacctgc tagctgttga ttcaagaaca ggcaaactca ctttgaaaaa taaagttacc   1560
aaggaacagt acaatatgct cggaggaaaa taccaaggaa cgattctctc tatagatgat   1620
aatcttcaaa gaacttgcac tggtacaatt aatattaaca ttcaaagttt tggtaatgac   1680
gacaggacta atacagagcc gaacactaaa attactacca atactggcag acaagaaagt   1740
acttcttcca ctaactatga taccagcaca acttctactg actctagcca agtatattct   1800
tctgaacccg gaaacggagc caaagatttg ttatcagaca atgtacattt tggtcctgct   1860
ggcattggac tcctcatcat gggattcttg gtcttaggat tggtcccatt tttgatgatc   1920
tgttgtgatt gtggaggtgc tcctcgtagt gcagctggct ttgagcctgt tcccgaatgt  1980
tcagatggag caattcattc atgggcagta gaaggaccac agcctgaacc cagggatata   2040
accactgtca taccacaaat accacctgat aacgcaaata taattgaatg cattgacaac   2100
tcaggagttt atacaaatga gtatggtggc agagaaatgc aagatctggg aggaggagag   2160
agaatgacag gatttgaact aacagaggga gttaaaactt caggaatgcc tgagatatgt   2220
caagaatact ctggaacatt aagaagaaat tctatgaggg aatgtagaga aggaggtctg   2280
aatatgaatt tcatggaaag ctacttctgt cagaaagcat atgcttacgc agatgaagat   2340
gaaggacgcc catctaatga ctgtttgctc atatatgaca tcgaaggtgt aggttccccct   2400 gctggctctg tgggttgttg tagcttcatt ggagaagacc tggatgacag cttcttggat   2460
```

-continued

```
acctgggac ctaaatttaa gaagttggca gacatcagcc taggaaaaga atcatatcca    2520
gaccttgatc cttcttggcc accacaaagc actgaaccag tttgccttcc tcaggaaaca    2580
gagcccgttg ttagtggaca cccaccaatc tccccacatt tcggcactac cacagtaatt    2640
tctgagagca cctatccctc gggacctggt gtactgcatc ctaagcctat tctcgatcct    2700
ctgggctatg gtaatgtcac tgtgaccgag tcttacacca cctctgacac tctgaagccc    2760
tctgtgcacg ttcacgataa ccgaccagca tcaaacgtgg tagtgacaga gagagtggtc    2820
ggcccaatct ctggcgctga tttgcatgga atgttagaga tgcctgactt gcgagatggg    2880
tcgaatgtta tagtgacaga aagggtaata gcaccaagct ctagtctacc cacctctctg    2940
actatccatc atcctagaga gtcttcaaat gtggtagtga cagaaagagt aatccaacca    3000
acttccggca tgataggtag tctgagtatg cacccccgagt tagccaatgc ccacaatgtc    3060
attgtgacag agagggttgt ttctggtgct ggcgtaactg gaattagtgg caccactggg    3120
atcagcggtg gcataggcag cagtggcctg gttggcacca gcatgggtgc tgggagcggt    3180
gccctgagtg gagctggcat aagtggtggt ggcattggcc tgagcagctt gggagggaca    3240
gccagcattg gccacatgag gagttcctct gaccatcact ttaaccaaac cattgggtcc    3300
gcctccccta gcacagctcg aagtcgaatc acaaagtata gtaccgtgca atatagcaag    3360
tagtcaggac cccagctcac ttttttcatag tcattgtggt ttagatccaa ttcccaccac    3420
taaaaaacta acaatgtgat ttataacgca caacttcgtg ctcaggtcat ctaggagcaa    3480
ggtgagaaat cacaatgaga aaaataaatg gaaacaccac tgctagggga gagctctcct    3540
tagcattcat aaacttttct cttatattag gactaaggaa ctaaaacttg aggcagagtc    3600
ttctttgtgc ctgagtggcc tgtagtccat ctccagcatg taactggcct tacgatggca    3660
attggcatca ttctccttgc tctgttttgc ttttccatat agctcgagca aaattcaaaa    3720
agaactaaat atgcaatata tgttcatatc tatgggaaaa atctaaaatg tgtgccagat    3780
gccctgttgg tttcacagat aacataaata aaaattcaac cacagattta tacaagggtt    3840
aaccattttt tttaagtttg actacatagt caagtccaca agccatcaag cactcctacc    3900
ttaattattg cactagagaa aataaattcc aaattaggaa gtgtttccta ggaggaaaat    3960
tccattagag agtggcaata ggatgaggtt tcttcagggt aaactagcaa tgcctgagcc    4020
tgaaccttaa tgtggggcct cagttaatat ccctgtggag tcaaggattc ttctgattct    4080
agtgtgtgtt tagtgataga tgtagtcttg acgaatattg cttactggtg aggttgagga    4140
atatcacact cgtctttccc tttaccactg tggttttgac ttaagaaagc aaaactcact    4200
aagtttactt ctcgaattga agcaagtgag gcctgacatg gttgtcatca ctagtggcaa    4260
atgaccttcc aagtaagcag atgggaactg aattgtgttt tcaggttttg tttttagtag    4320
gtgatattca ttcgtatcca gctctttatt acatagctct gaagttaaaa tgatttacat    4380
aggccgagct gtggacaaaa aaaagaagc agcagcttgt agtatgctta agctttgggg    4440 aattttttt taagggatc taaaaaaatg tttttagaac atgtaaaatg tttaatggtg    4500
aaagttggaa aa                                                      4512
```

<210> SEQ ID NO 2
<211> LENGTH: 1049
<212> TYPE: PRT
<213> ORGANISM: Homo Sapiens

<400> SEQUENCE: 2

```
Met Asp Trp Ser Phe Phe Arg Val Val Ala Val Leu Phe Ile Phe Leu
1               5                   10                  15

Val Val Val Glu Val Asn Ser Glu Phe Arg Ile Gln Val Arg Asp Tyr
            20                  25                  30

Asn Thr Lys Asn Gly Thr Ile Lys Trp His Ser Ile Arg Arg Gln Lys
            35                  40                  45

Arg Glu Trp Ile Lys Phe Ala Ala Cys Arg Glu Gly Glu Asp Asn
    50                  55                  60

Ser Lys Arg Asn Pro Ile Ala Lys Ile His Ser Asp Cys Ala Ala Asn
65                  70                  75                  80

Gln Gln Val Thr Tyr Arg Ile Ser Gly Val Gly Ile Asp Gln Pro Pro
                85                  90                  95

Tyr Gly Ile Phe Val Ile Asn Gln Lys Thr Gly Glu Ile Asn Ile Thr
                100                 105                 110

Ser Ile Val Asp Arg Glu Val Thr Pro Phe Phe Ile Ile Tyr Cys Arg
            115                 120                 125

Ala Leu Asn Ser Met Gly Gln Asp Leu Glu Arg Pro Leu Glu Leu Arg
130                 135                 140

Val Arg Val Leu Asp Ile Asn Asp Asn Pro Pro Val Phe Ser Met Ala
145                 150                 155                 160

Thr Phe Ala Gly Gln Ile Glu Glu Asn Ser Asn Ala Asn Thr Leu Val
                165                 170                 175

Met Ile Leu Asn Ala Thr Asp Ala Asp Glu Pro Asn Asn Leu Asn Ser
            180                 185                 190

Lys Ile Ala Phe Lys Ile Ile Arg Gln Glu Pro Ser Asp Ser Pro Met
        195                 200                 205

Phe Ile Ile Asn Arg Asn Thr Gly Glu Ile Arg Thr Met Asn Asn Phe
210                 215                 220

Leu Asp Arg Glu Gln Tyr Gly Gln Tyr Ala Leu Ala Val Arg Gly Ser
225                 230                 235                 240

Asp Arg Asp Gly Gly Ala Asp Gly Met Ser Ala Glu Cys Glu Cys Asn
                245                 250                 255

Ile Lys Ile Leu Asp Val Asn Asp Asn Ile Pro Tyr Met Glu Gln Ser
            260                 265                 270

Ser Tyr Thr Ile Glu Ile Gln Glu Asn Thr Leu Asn Ser Asn Leu Leu
        275                 280                 285

Glu Ile Arg Val Ile Asp Leu Asp Glu Glu Phe Ser Ala Asn Trp Met
290                 295                 300

Ala Val Ile Phe Phe Ile Ser Gly Asn Glu Gly Asn Trp Phe Glu Ile
305                 310                 315                 320

Glu Met Asn Glu Arg Thr Asn Val Gly Ile Leu Lys Val Val Lys Pro
                325                 330                 335

Leu Asp Tyr Glu Ala Met Gln Ser Leu Gln Leu Ser Ile Gly Val Arg
            340                 345                 350

Asn Lys Ala Glu Phe His His Ser Ile Met Ser Gln Tyr Lys Leu Lys
        355                 360                 365

Ala Ser Ala Ile Ser Val Thr Val Leu Asn Val Ile Glu Gly Pro Val
370                 375                 380

Phe Arg Pro Gly Ser Lys Thr Tyr Val Val Thr Gly Asn Met Gly Ser
385                 390                 395                 400

Asn Asp Lys Val Gly Asp Phe Val Ala Thr Asp Leu Asp Thr Gly Arg
                405                 410                 415
```

```
Pro Ser Thr Thr Val Arg Tyr Val Met Gly Asn Asn Pro Ala Asp Leu
            420                 425                 430

Leu Ala Val Asp Ser Arg Thr Gly Lys Leu Thr Leu Lys Asn Lys Val
        435                 440                 445

Thr Lys Glu Gln Tyr Asn Met Leu Gly Gly Lys Tyr Gln Gly Thr Ile
    450                 455                 460

Leu Ser Ile Asp Asp Asn Leu Gln Arg Thr Cys Thr Gly Thr Ile Asn
465                 470                 475                 480

Ile Asn Ile Gln Ser Phe Gly Asn Asp Asp Arg Thr Asn Thr Glu Pro
                485                 490                 495

Asn Thr Lys Ile Thr Thr Asn Thr Gly Arg Gln Glu Ser Thr Ser Ser
            500                 505                 510

Thr Asn Tyr Asp Thr Ser Thr Thr Ser Thr Asp Ser Ser Gln Val Tyr
        515                 520                 525

Ser Ser Glu Pro Gly Asn Gly Ala Lys Asp Leu Leu Ser Asp Asn Val
    530                 535                 540

His Phe Gly Pro Ala Gly Ile Gly Leu Leu Ile Met Gly Phe Leu Val
545                 550                 555                 560

Leu Gly Leu Val Pro Phe Leu Met Ile Cys Cys Asp Cys Gly Gly Ala
                565                 570                 575

Pro Arg Ser Ala Ala Gly Phe Glu Pro Val Pro Glu Cys Ser Asp Gly
            580                 585                 590

Ala Ile His Ser Trp Ala Val Glu Gly Pro Gln Pro Glu Pro Arg Asp
        595                 600                 605

Ile Thr Thr Val Ile Pro Gln Ile Pro Pro Asp Asn Ala Asn Ile Ile
    610                 615                 620

Glu Cys Ile Asp Asn Ser Gly Val Tyr Thr Asn Glu Tyr Gly Gly Arg
625                 630                 635                 640

Glu Met Gln Asp Leu Gly Gly Glu Arg Met Thr Gly Phe Glu Leu
                645                 650                 655

Thr Glu Gly Val Lys Thr Ser Gly Met Pro Glu Ile Cys Gln Glu Tyr
            660                 665                 670

Ser Gly Thr Leu Arg Arg Asn Ser Met Arg Glu Cys Arg Glu Gly Gly
        675                 680                 685

Leu Asn Met Asn Phe Met Glu Ser Tyr Phe Cys Gln Lys Ala Tyr Ala
    690                 695                 700

Tyr Ala Asp Glu Asp Glu Gly Arg Pro Ser Asn Asp Cys Leu Leu Ile
705                 710                 715                 720

Tyr Asp Ile Glu Gly Val Gly Ser Pro Ala Gly Ser Val Gly Cys Cys
                725                 730                 735

Ser Phe Ile Gly Glu Asp Leu Asp Asp Ser Phe Leu Asp Thr Leu Gly
            740                 745                 750

Pro Lys Phe Lys Lys Leu Ala Asp Ile Ser Leu Gly Lys Glu Ser Tyr
        755                 760                 765

Pro Asp Leu Asp Pro Ser Trp Pro Pro Gln Ser Thr Glu Pro Val Cys
    770                 775                 780

Leu Pro Gln Glu Thr Glu Pro Val Val Ser Gly His Pro Pro Ile Ser
785                 790                 795                 800

Pro His Phe Gly Thr Thr Thr Val Ile Ser Glu Ser Thr Tyr Pro Ser
                805                 810                 815

Gly Pro Gly Val Leu His Pro Lys Pro Ile Leu Asp Pro Leu Gly Tyr
            820                 825                 830
```

```
Gly Asn Val Thr Val Thr Glu Ser Tyr Thr Thr Ser Asp Thr Leu Lys
            835                 840                 845

Pro Ser Val His Val His Asp Asn Arg Pro Ala Ser Asn Val Val Val
    850                 855                 860

Thr Glu Arg Val Val Gly Pro Ile Ser Gly Ala Asp Leu His Gly Met
865                 870                 875                 880

Leu Glu Met Pro Asp Leu Arg Asp Gly Ser Asn Val Ile Val Thr Glu
                885                 890                 895

Arg Val Ile Ala Pro Ser Ser Ser Leu Pro Thr Ser Leu Thr Ile His
                900                 905                 910

His Pro Arg Glu Ser Ser Asn Val Val Val Thr Glu Arg Val Ile Gln
            915                 920                 925

Pro Thr Ser Gly Met Ile Gly Ser Leu Ser Met His Pro Glu Leu Ala
            930                 935                 940

Asn Ala His Asn Val Ile Val Thr Glu Arg Val Val Ser Gly Ala Gly
945                 950                 955                 960

Val Thr Gly Ile Ser Gly Thr Thr Gly Ile Ser Gly Gly Ile Gly Ser
                965                 970                 975

Ser Gly Leu Val Gly Thr Ser Met Gly Ala Gly Ser Gly Ala Leu Ser
                980                 985                 990

Gly Ala Gly Ile Ser Gly Gly Ile Gly Leu Ser Ser Leu Gly Gly
            995                 1000                1005

Thr Ala  Ser Ile Gly His Met  Arg Ser Ser Ser Asp  His His Phe
             1010                 1015                1020

Asn Gln  Thr Ile Gly Ser Ala  Ser Pro Ser Thr Ala  Arg Ser Arg
    1025                 1030                1035

Ile Thr  Lys Tyr Ser Thr Val  Gln Tyr Ser Lys
             1040                 1045

<210> SEQ ID NO 3
<211> LENGTH: 8
<212> TYPE: PRT
<213> ORGANISM: Homo Sapiens

<400> SEQUENCE: 3

Ala Glu Phe His His Ser Ile Met
1               5

<210> SEQ ID NO 4
<211> LENGTH: 12
<212> TYPE: PRT
<213> ORGANISM: Homo Sapiens

<400> SEQUENCE: 4

Ala Glu Phe His His Ser Ile Met Ser Gln Tyr Lys
1               5                   10

<210> SEQ ID NO 5
<211> LENGTH: 13
<212> TYPE: PRT
<213> ORGANISM: Homo Sapiens

<400> SEQUENCE: 5

Ala Gly Gln Ile Glu Glu Asn Ser Asn Ala Asn Thr Leu
1               5                   10
```

```
<210> SEQ ID NO 6
<211> LENGTH: 14
<212> TYPE: PRT
<213> ORGANISM: Homo Sapiens

<400> SEQUENCE: 6

Ala Gly Gln Ile Glu Glu Asn Ser Asn Ala Asn Thr Leu Val
1               5                   10

<210> SEQ ID NO 7
<211> LENGTH: 16
<212> TYPE: PRT
<213> ORGANISM: Homo Sapiens

<400> SEQUENCE: 7

Ala Leu Asn Ser Met Gly Gln Asp Leu Glu Arg Pro Leu Glu Leu Arg
1               5                   10                  15

<210> SEQ ID NO 8
<211> LENGTH: 18
<212> TYPE: PRT
<213> ORGANISM: Homo Sapiens

<400> SEQUENCE: 8

Ala Ser Ala Ile Ser Val Thr Val Leu Asn Val Ile Glu Gly Pro Val
1               5                   10                  15

Phe Arg

<210> SEQ ID NO 9
<211> LENGTH: 22
<212> TYPE: PRT
<213> ORGANISM: Homo Sapiens

<400> SEQUENCE: 9

Ala Ser Ala Ile Ser Val Thr Val Leu Asn Val Ile Glu Gly Pro Val
1               5                   10                  15

Phe Arg Pro Gly Ser Lys
            20

<210> SEQ ID NO 10
<211> LENGTH: 16
<212> TYPE: PRT
<213> ORGANISM: Homo Sapiens

<400> SEQUENCE: 10

Asp Gly Gly Ala Asp Gly Met Ser Ala Glu Cys Glu Cys Asn Ile Lys
1               5                   10                  15

<210> SEQ ID NO 11
<211> LENGTH: 17
<212> TYPE: PRT
<213> ORGANISM: Homo Sapiens

<400> SEQUENCE: 11

Asp Gly Gly Ala Asp Gly Met Ser Ala Glu Cys Glu Cys Asn Ile Lys
1               5                   10                  15

Ile

<210> SEQ ID NO 12
<211> LENGTH: 18
<212> TYPE: PRT
<213> ORGANISM: Homo Sapiens
```

```
<400> SEQUENCE: 12

Asp Gly Gly Ala Asp Gly Met Ser Ala Glu Cys Glu Cys Asn Ile Lys
1               5                   10                  15

Ile Leu

<210> SEQ ID NO 13
<211> LENGTH: 13
<212> TYPE: PRT
<213> ORGANISM: Homo Sapiens

<400> SEQUENCE: 13

Asp Ile Asn Asp Asn Pro Pro Val Phe Ser Met Ala Thr
1               5                   10

<210> SEQ ID NO 14
<211> LENGTH: 12
<212> TYPE: PRT
<213> ORGANISM: Homo Sapiens

<400> SEQUENCE: 14

Asp Leu Asp Thr Gly Arg Pro Ser Thr Thr Val Arg
1               5                   10

<210> SEQ ID NO 15
<211> LENGTH: 9
<212> TYPE: PRT
<213> ORGANISM: Homo Sapiens

<400> SEQUENCE: 15

Asp Ser Pro Met Phe Ile Ile Asn Arg
1               5

<210> SEQ ID NO 16
<211> LENGTH: 11
<212> TYPE: PRT
<213> ORGANISM: Homo Sapiens

<400> SEQUENCE: 16

Glu Ile Arg Val Ile Asp Leu Asp Glu Glu Phe
1               5                   10

<210> SEQ ID NO 17
<211> LENGTH: 14
<212> TYPE: PRT
<213> ORGANISM: Homo Sapiens

<400> SEQUENCE: 17

Glu Ile Arg Val Ile Asp Leu Asp Glu Glu Phe Ser Ala Asn
1               5                   10

<210> SEQ ID NO 18
<211> LENGTH: 11
<212> TYPE: PRT
<213> ORGANISM: Homo Sapiens

<400> SEQUENCE: 18

Glu Gln Tyr Gly Gln Tyr Ala Leu Ala Val Arg
1               5                   10

<210> SEQ ID NO 19
<211> LENGTH: 9
<212> TYPE: PRT
<213> ORGANISM: Homo Sapiens
```

```
<400> SEQUENCE: 19

Glu Gln Tyr Asn Met Leu Gly Gly Lys
1               5

<210> SEQ ID NO 20
<211> LENGTH: 10
<212> TYPE: PRT
<213> ORGANISM: Homo Sapiens

<400> SEQUENCE: 20

Glu Ser Ser Asn Val Val Thr Glu Arg
1               5                   10

<210> SEQ ID NO 21
<211> LENGTH: 11
<212> TYPE: PRT
<213> ORGANISM: Homo Sapiens

<400> SEQUENCE: 21

Glu Val Thr Pro Phe Phe Ile Ile Tyr Cys Arg
1               5                   10

<210> SEQ ID NO 22
<211> LENGTH: 13
<212> TYPE: PRT
<213> ORGANISM: Homo Sapiens

<400> SEQUENCE: 22

Phe Ile Ser Gly Asn Glu Gly Asn Trp Phe Glu Ile Glu
1               5                   10

<210> SEQ ID NO 23
<211> LENGTH: 16
<212> TYPE: PRT
<213> ORGANISM: Homo Sapiens

<400> SEQUENCE: 23

Phe Leu Val Leu Gly Leu Val Pro Phe Leu Met Ile Cys Cys Asp Cys
1               5                   10                  15

<210> SEQ ID NO 24
<211> LENGTH: 17
<212> TYPE: PRT
<213> ORGANISM: Homo Sapiens

<400> SEQUENCE: 24

Phe Leu Val Leu Gly Leu Val Pro Phe Leu Met Ile Cys Cys Asp Cys
1               5                   10                  15

Gly

<210> SEQ ID NO 25
<211> LENGTH: 18
<212> TYPE: PRT
<213> ORGANISM: Homo Sapiens

<400> SEQUENCE: 25

Phe Leu Val Leu Gly Leu Val Pro Phe Leu Met Ile Cys Cys Asp Cys
1               5                   10                  15

Gly Gly
```

```
<210> SEQ ID NO 26
<211> LENGTH: 17
<212> TYPE: PRT
<213> ORGANISM: Homo Sapiens

<400> SEQUENCE: 26

Gly Val Gly Ile Asp Gln Pro Pro Tyr Gly Ile Phe Val Ile Asn Gln
1               5                   10                  15

Lys

<210> SEQ ID NO 27
<211> LENGTH: 14
<212> TYPE: PRT
<213> ORGANISM: Homo Sapiens

<400> SEQUENCE: 27

Ile His Ser Asp Cys Ala Ala Asn Gln Gln Val Thr Tyr Arg
1               5                   10

<210> SEQ ID NO 28
<211> LENGTH: 16
<212> TYPE: PRT
<213> ORGANISM: Homo Sapiens

<400> SEQUENCE: 28

Ile Ile Arg Gln Glu Pro Ser Asp Ser Pro Met Phe Ile Ile Asn Arg
1               5                   10                  15

<210> SEQ ID NO 29
<211> LENGTH: 10
<212> TYPE: PRT
<213> ORGANISM: Homo Sapiens

<400> SEQUENCE: 29

Ile Leu Asp Val Asn Asp Asn Ile Pro Tyr
1               5                   10

<210> SEQ ID NO 30
<211> LENGTH: 10
<212> TYPE: PRT
<213> ORGANISM: Homo Sapiens

<400> SEQUENCE: 30

Ile Leu Ser Ile Asp Asp Asn Leu Gln Arg
1               5                   10

<210> SEQ ID NO 31
<211> LENGTH: 19
<212> TYPE: PRT
<213> ORGANISM: Homo Sapiens

<400> SEQUENCE: 31

Ile Ser Gly Val Gly Ile Asp Gln Pro Pro Tyr Gly Ile Phe Val Ile
1               5                   10                  15

Asn Gln Lys

<210> SEQ ID NO 32
<211> LENGTH: 16
<212> TYPE: PRT
<213> ORGANISM: Homo Sapiens

<400> SEQUENCE: 32

Lys Ile Ile Arg Gln Glu Pro Ser Asp Ser Pro Met Phe Ile Ile Asn
1               5                   10                  15
```

<210> SEQ ID NO 33
<211> LENGTH: 17
<212> TYPE: PRT
<213> ORGANISM: Homo Sapiens

<400> SEQUENCE: 33

Lys Ile Ile Arg Gln Glu Pro Ser Asp Ser Pro Met Phe Ile Ile Asn
1               5                   10                  15
Arg

<210> SEQ ID NO 34
<211> LENGTH: 11
<212> TYPE: PRT
<213> ORGANISM: Homo Sapiens

<400> SEQUENCE: 34

Lys Leu Lys Ala Ser Ala Ile Ser Val Thr Val
1               5                   10

<210> SEQ ID NO 35
<211> LENGTH: 12
<212> TYPE: PRT
<213> ORGANISM: Homo Sapiens

<400> SEQUENCE: 35

Lys Leu Lys Ala Ser Ala Ile Ser Val Thr Val Leu
1               5                   10

<210> SEQ ID NO 36
<211> LENGTH: 8
<212> TYPE: PRT
<213> ORGANISM: Homo Sapiens

<400> SEQUENCE: 36

Leu Ala Asp Ile Ser Leu Gly Lys
1               5

<210> SEQ ID NO 37
<211> LENGTH: 9
<212> TYPE: PRT
<213> ORGANISM: Homo Sapiens

<400> SEQUENCE: 37

Leu Asp Arg Glu Gln Tyr Gly Gln Tyr
1               5

<210> SEQ ID NO 38
<211> LENGTH: 11
<212> TYPE: PRT
<213> ORGANISM: Homo Sapiens

<400> SEQUENCE: 38

Asn Met Leu Gly Gly Lys Tyr Gln Gly Thr Ile
1               5                   10

<210> SEQ ID NO 39
<211> LENGTH: 12
<212> TYPE: PRT
<213> ORGANISM: Homo Sapiens

<400> SEQUENCE: 39

Asn Met Leu Gly Gly Lys Tyr Gln Gly Thr Ile Leu
1               5                   10

```
<210> SEQ ID NO 40
<211> LENGTH: 9
<212> TYPE: PRT
<213> ORGANISM: Homo Sapiens

<400> SEQUENCE: 40

Asn Asn Phe Leu Asp Arg Glu Gln Tyr
1               5

<210> SEQ ID NO 41
<211> LENGTH: 10
<212> TYPE: PRT
<213> ORGANISM: Homo Sapiens

<400> SEQUENCE: 41

Asn Asn Phe Leu Asp Arg Glu Gln Tyr Gly
1               5                   10

<210> SEQ ID NO 42
<211> LENGTH: 11
<212> TYPE: PRT
<213> ORGANISM: Homo Sapiens

<400> SEQUENCE: 42

Asn Asn Phe Leu Asp Arg Glu Gln Tyr Gly Gln
1               5                   10

<210> SEQ ID NO 43
<211> LENGTH: 12
<212> TYPE: PRT
<213> ORGANISM: Homo Sapiens

<400> SEQUENCE: 43

Asn Asn Phe Leu Asp Arg Glu Gln Tyr Gly Gln Tyr
1               5                   10

<210> SEQ ID NO 44
<211> LENGTH: 8
<212> TYPE: PRT
<213> ORGANISM: Homo Sapiens

<400> SEQUENCE: 44

Asn Ser Asn Leu Leu Glu Ile Arg
1               5

<210> SEQ ID NO 45
<211> LENGTH: 9
<212> TYPE: PRT
<213> ORGANISM: Homo Sapiens

<400> SEQUENCE: 45

Asn Val Ile Glu Gly Pro Val Phe Arg
1               5

<210> SEQ ID NO 46
<211> LENGTH: 12
<212> TYPE: PRT
<213> ORGANISM: Homo Sapiens

<400> SEQUENCE: 46

Asn Val Ile Glu Gly Pro Val Phe Arg Pro Gly Ser
1               5                   10
```

```
<210> SEQ ID NO 47
<211> LENGTH: 13
<212> TYPE: PRT
<213> ORGANISM: Homo Sapiens

<400> SEQUENCE: 47

Asn Val Ile Glu Gly Pro Val Phe Arg Pro Gly Ser Lys
1               5                   10

<210> SEQ ID NO 48
<211> LENGTH: 14
<212> TYPE: PRT
<213> ORGANISM: Homo Sapiens

<400> SEQUENCE: 48

Asn Val Ile Glu Gly Pro Val Phe Arg Pro Gly Ser Lys Thr
1               5                   10

<210> SEQ ID NO 49
<211> LENGTH: 15
<212> TYPE: PRT
<213> ORGANISM: Homo Sapiens

<400> SEQUENCE: 49

Asn Val Ile Glu Gly Pro Val Phe Arg Pro Gly Ser Lys Thr Tyr
1               5                   10                  15

<210> SEQ ID NO 50
<211> LENGTH: 11
<212> TYPE: PRT
<213> ORGANISM: Homo Sapiens

<400> SEQUENCE: 50

Pro Pro Tyr Gly Ile Phe Val Ile Asn Gln Lys
1               5                   10

<210> SEQ ID NO 51
<211> LENGTH: 13
<212> TYPE: PRT
<213> ORGANISM: Homo Sapiens

<400> SEQUENCE: 51

Gln Glu Pro Ser Asp Ser Pro Met Phe Ile Ile Asn Arg
1               5                   10

<210> SEQ ID NO 52
<211> LENGTH: 11
<212> TYPE: PRT
<213> ORGANISM: Homo Sapiens

<400> SEQUENCE: 52

Arg Ile Ser Gly Val Gly Ile Asp Gln Pro Pro
1               5                   10

<210> SEQ ID NO 53
<211> LENGTH: 12
<212> TYPE: PRT
<213> ORGANISM: Homo Sapiens

<400> SEQUENCE: 53

Arg Ile Ser Gly Val Gly Ile Asp Gln Pro Pro Tyr
1               5                   10
```

```
<210> SEQ ID NO 54
<211> LENGTH: 13
<212> TYPE: PRT
<213> ORGANISM: Homo Sapiens

<400> SEQUENCE: 54

Arg Ile Ser Gly Val Gly Ile Asp Gln Pro Pro Tyr Gly
1               5                   10

<210> SEQ ID NO 55
<211> LENGTH: 14
<212> TYPE: PRT
<213> ORGANISM: Homo Sapiens

<400> SEQUENCE: 55

Arg Ile Ser Gly Val Gly Ile Asp Gln Pro Pro Tyr Gly Ile
1               5                   10

<210> SEQ ID NO 56
<211> LENGTH: 15
<212> TYPE: PRT
<213> ORGANISM: Homo Sapiens

<400> SEQUENCE: 56

Arg Ile Ser Gly Val Gly Ile Asp Gln Pro Pro Tyr Gly Ile Phe
1               5                   10                  15

<210> SEQ ID NO 57
<211> LENGTH: 8
<212> TYPE: PRT
<213> ORGANISM: Homo Sapiens

<400> SEQUENCE: 57

Ser Ile Asp Asp Asn Leu Gln Arg
1               5

<210> SEQ ID NO 58
<211> LENGTH: 10
<212> TYPE: PRT
<213> ORGANISM: Homo Sapiens

<400> SEQUENCE: 58

Ser Ile Val Asp Arg Glu Val Thr Pro Phe
1               5                   10

<210> SEQ ID NO 59
<211> LENGTH: 12
<212> TYPE: PRT
<213> ORGANISM: Homo Sapiens

<400> SEQUENCE: 59

Thr Ser Ile Val Asp Arg Glu Val Thr Pro Phe Phe
1               5                   10

<210> SEQ ID NO 60
<211> LENGTH: 17
<212> TYPE: PRT
<213> ORGANISM: Homo Sapiens

<400> SEQUENCE: 60

Thr Ile Glu Ile Gln Glu Asn Thr Leu Asn Ser Asn Leu Leu Glu Ile
1               5                   10                  15

Arg
```

```
<210> SEQ ID NO 61
<211> LENGTH: 10
<212> TYPE: PRT
<213> ORGANISM: Homo Sapiens

<400> SEQUENCE: 61

Thr Leu Asn Ser Asn Leu Leu Glu Ile Arg
1               5                   10

<210> SEQ ID NO 62
<211> LENGTH: 8
<212> TYPE: PRT
<213> ORGANISM: Homo Sapiens

<400> SEQUENCE: 62

Thr Met Asn Asn Phe Leu Asp Arg
1               5

<210> SEQ ID NO 63
<211> LENGTH: 13
<212> TYPE: PRT
<213> ORGANISM: Homo Sapiens

<400> SEQUENCE: 63

Thr Tyr Val Val Thr Gly Asn Met Gly Ser Asn Asp Lys
1               5                   10

<210> SEQ ID NO 64
<211> LENGTH: 12
<212> TYPE: PRT
<213> ORGANISM: Homo Sapiens

<400> SEQUENCE: 64

Val Ala Thr Asp Leu Asp Thr Gly Arg Pro Ser Thr
1               5                   10

<210> SEQ ID NO 65
<211> LENGTH: 14
<212> TYPE: PRT
<213> ORGANISM: Homo Sapiens

<400> SEQUENCE: 65

Val Ala Thr Asp Leu Asp Thr Gly Arg Pro Ser Thr Thr Val
1               5                   10

<210> SEQ ID NO 66
<211> LENGTH: 15
<212> TYPE: PRT
<213> ORGANISM: Homo Sapiens

<400> SEQUENCE: 66

Val Ala Thr Asp Leu Asp Thr Gly Arg Pro Ser Thr Thr Val Arg
1               5                   10                  15

<210> SEQ ID NO 67
<211> LENGTH: 19
<212> TYPE: PRT
<213> ORGANISM: Homo Sapiens

<400> SEQUENCE: 67

Val Gly Asp Phe Val Ala Thr Asp Leu Asp Thr Gly Arg Pro Ser Thr
1               5                   10                  15

Thr Val Arg
```

```
<210> SEQ ID NO 68
<211> LENGTH: 11
<212> TYPE: PRT
<213> ORGANISM: Homo Sapiens

<400> SEQUENCE: 68

Val Ile Asp Leu Asp Glu Glu Phe Ser Ala Asn
1               5                   10

<210> SEQ ID NO 69
<211> LENGTH: 29
<212> TYPE: PRT
<213> ORGANISM: Homo Sapiens

<400> SEQUENCE: 69

Val Ile Gln Pro Thr Ser Gly Met Ile Gly Ser Leu Ser Met His Pro
1               5                   10                  15

Glu Leu Ala Asn Ala His Asn Val Ile Val Thr Glu Arg
            20                  25

<210> SEQ ID NO 70
<211> LENGTH: 10
<212> TYPE: PRT
<213> ORGANISM: Homo Sapiens

<400> SEQUENCE: 70

Val Leu Asp Ile Asn Asp Asn Pro Pro Val
1               5                   10

<210> SEQ ID NO 71
<211> LENGTH: 13
<212> TYPE: PRT
<213> ORGANISM: Homo Sapiens

<400> SEQUENCE: 71

Val Leu Asp Ile Asn Asp Asn Pro Pro Val Phe Ser Met
1               5                   10

<210> SEQ ID NO 72
<211> LENGTH: 14
<212> TYPE: PRT
<213> ORGANISM: Homo Sapiens

<400> SEQUENCE: 72

Val Leu Asp Ile Asn Asp Asn Pro Pro Val Phe Ser Met Ala
1               5                   10

<210> SEQ ID NO 73
<211> LENGTH: 11
<212> TYPE: PRT
<213> ORGANISM: Homo Sapiens

<400> SEQUENCE: 73

Val Leu Asn Val Ile Glu Gly Pro Val Phe Arg
1               5                   10

<210> SEQ ID NO 74
<211> LENGTH: 10
<212> TYPE: PRT
<213> ORGANISM: Homo Sapiens

<400> SEQUENCE: 74

Val Met Gly Asn Asn Pro Ala Asp Leu Leu
1               5                   10
```

```
<210> SEQ ID NO 75
<211> LENGTH: 15
<212> TYPE: PRT
<213> ORGANISM: Homo Sapiens

<400> SEQUENCE: 75

Val Met Gly Asn Asn Pro Ala Asp Leu Leu Ala Val Asp Ser Arg
1               5                   10                  15

<210> SEQ ID NO 76
<211> LENGTH: 18
<212> TYPE: PRT
<213> ORGANISM: Homo Sapiens

<400> SEQUENCE: 76

Val Met Gly Asn Asn Pro Ala Asp Leu Leu Ala Val Asp Ser Arg Thr
1               5                   10                  15

Gly Lys

<210> SEQ ID NO 77
<211> LENGTH: 20
<212> TYPE: PRT
<213> ORGANISM: Homo Sapiens

<400> SEQUENCE: 77

Val Met Gly Asn Asn Pro Ala Asp Leu Leu Ala Val Asp Ser Arg Thr
1               5                   10                  15

Gly Lys Leu Thr
            20

<210> SEQ ID NO 78
<211> LENGTH: 20
<212> TYPE: PRT
<213> ORGANISM: Homo Sapiens

<400> SEQUENCE: 78

Val Val Lys Pro Leu Asp Tyr Glu Ala Met Gln Ser Leu Gln Leu Ser
1               5                   10                  15

Ile Gly Val Arg
            20

<210> SEQ ID NO 79
<211> LENGTH: 11
<212> TYPE: PRT
<213> ORGANISM: Homo Sapiens

<400> SEQUENCE: 79

Val Val Thr Gly Asn Met Gly Ser Asn Asp Lys
1               5                   10

<210> SEQ ID NO 80
<211> LENGTH: 15
<212> TYPE: PRT
<213> ORGANISM: Homo Sapiens

<400> SEQUENCE: 80

Val Val Thr Gly Asn Met Gly Ser Asn Asp Lys Val Gly Asp Phe
1               5                   10                  15

<210> SEQ ID NO 81
<211> LENGTH: 18
<212> TYPE: PRT
<213> ORGANISM: Homo Sapiens
```

```
<400> SEQUENCE: 81

Val Val Thr Gly Asn Met Gly Ser Asn Asp Lys Val Gly Asp Phe Val
1               5                   10                  15

Ala Thr

<210> SEQ ID NO 82
<211> LENGTH: 20
<212> TYPE: PRT
<213> ORGANISM: Homo Sapiens

<400> SEQUENCE: 82

Val Val Thr Gly Asn Met Gly Ser Asn Asp Lys Val Gly Asp Phe Val
1               5                   10                  15

Ala Thr Asp Leu
        20

<210> SEQ ID NO 83
<211> LENGTH: 30
<212> TYPE: PRT
<213> ORGANISM: Homo Sapiens

<400> SEQUENCE: 83

Val Val Thr Gly Asn Met Gly Ser Asn Asp Lys Val Gly Asp Phe Val
1               5                   10                  15

Ala Thr Asp Leu Asp Thr Gly Arg Pro Ser Thr Thr Val Arg
        20                  25                  30

<210> SEQ ID NO 84
<211> LENGTH: 14
<212> TYPE: PRT
<213> ORGANISM: Homo Sapiens

<400> SEQUENCE: 84

Tyr Gln Gly Thr Ile Leu Ser Ile Asp Asp Asn Leu Gln Arg
1               5                   10

<210> SEQ ID NO 85
<211> LENGTH: 16
<212> TYPE: PRT
<213> ORGANISM: Homo Sapiens

<400> SEQUENCE: 85

Tyr Val Met Gly Asn Asn Pro Ala Asp Leu Leu Ala Val Asp Ser Arg
1               5                   10                  15
```